United States Patent
Mukhopadhyay et al.

(10) Patent No.: US 7,135,601 B2
(45) Date of Patent: Nov. 14, 2006

(54) CATALYTIC METHOD FOR THE PRODUCTION OF FLUOROALKYLENES FROM CHLOROFLUOROHYDROCARBONS

(75) Inventors: Sudip Mukhopadhyay, Buffalo, NY (US); HsuehSung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 126 days.

(21) Appl. No.: 11/091,201

(22) Filed: Mar. 28, 2005

(65) Prior Publication Data

US 2006/0217577 A1 Sep. 28, 2006

(51) Int. Cl.
*C07C 21/00* (2006.01)

(52) U.S. Cl. .................. 570/226; 570/227; 570/136; 570/153

(58) Field of Classification Search .................. 570/1, 570/23, 175, 216, 226, 227
See application file for complete search history.

(56) References Cited

U.S. PATENT DOCUMENTS

| 4,935,558 A | * | 6/1990 | Krespan et al. ............. 570/176 |
| 5,892,135 A |   | 4/1999 | Manogue et al. |

FOREIGN PATENT DOCUMENTS

| CN | 1351903 A | 6/2002 |
| EP | 747337 | 12/1996 |
| FR | 2729136 | 7/1996 |
| JP | 43008454 | 4/1968 |
| JP | 2002275106 | 9/2002 |
| RU | 2188814 C | 9/2002 |
| WO | WO9729062 A1 | 8/1997 |
| WO | WO 2004/080937 A1 * | 9/2004 |
| WO | WO2004080937 | 9/2004 |

OTHER PUBLICATIONS

Journal of Electroanalytical Chemistry 1997, 435 (1-2), 255-258, Abstract.

* cited by examiner

*Primary Examiner*—Johann Richter
*Assistant Examiner*—Karl Puttlitz
(74) *Attorney, Agent, or Firm*—Colleen D. Szuch

(57) ABSTRACT

A process for producing a producing a product of the formula:

$$R\text{—}CF\text{=}CHR^1$$

wherein R is F or $CF_3$ and $R^1$ is F when R is F and is H when R is $CF_3$ by reacting a reactant of the formula:

$$CF_3\text{—}R^2$$

wherein $R^2$ is selected from $$\underset{|}{\overset{R^3}{\text{—CFCL}}}$$

and $$\underset{|}{\overset{R^4}{\text{—CF}_2\text{—CHCl}}}$$

wherein $R^3$ is H, F or Cl and $R^4$ is H or Cl,
in the presence of a suitable catalyst, with a reducing agent selected from methane, methyl chloride and mixtures thereof, in a gas phase reaction.

20 Claims, No Drawings

CATALYTIC METHOD FOR THE PRODUCTION OF FLUOROALKYLENES FROM CHLOROFLUOROHYDROCARBONS

1. FIELD OF THE INVENTION

This invention relates to a more cost effective catalytic method for producing trifluoroethylene (R1123) or tetrafluoropropylene (R1234yf) from the relatively inexpensive and readily available feedstock materials.

2. BACKGROUND TO THE INVENTION

Trifluoroethylene, $CF_2$=CHF or R1123, and 1,1,1,2-tetrafluoropropene, $CF_3$—CF=$CH_2$ or R1234yf, are very useful, high-priced, high-demand monomers for the preparation of fluorocarbon polymers. The need for trifluoroethylene and tetrafluoropropylene as a monomer for producing fluorocarbon polymers has enormous growth potential as the need for fluorocarbon polymers is expected to grow rapidly.

There is, however, no cost effective and simple way to produce trifluoroethylene (R1123) and tetrafluoropropylene (R1234yf). Trifluoroethylene can be produced from $CCl_2FCClF_2$ (R113) by reaction with hydrogen in the presence of a catalyst comprising palladium and at least one other metal selected from gold, tellurium, antimony, bismuth and arsenic as disclosed in U.S. Pat. No. 5,283,379. Trifluoroethylene can also be prepared from $CF_2$=CClF (R1113) by reaction with hydrogen in the presence of a catalyst comprising palladium or platinum on a magnesium oxide carrier as disclosed in U.S. Pat. No. 5,089,454. In U.S. Pat. No. 5,892,135 it is disclosed that trifluoroethylene is prepared. in high yield and selectivity by contacting, in the vapor phase, at least one halogenated ethane $CF_3CClFX$ where X=H, Cl or F, e.g., 2,2-dichloro-1,1,1,2-tetrafluoroethane, by reaction with hydrogen in the presence of a catalyst comprising at least one component selected from metals, metal oxides, metal halides, and metal oxyhalides of ruthenium, copper, nickel, and/or chromium and the halogen of the halides and the oxyhalides is fluorine and/or chlorine. European Patent Publication No. 0 747 337 A1 disclosed a process for the preparation of chlorotrifluoroethylene and trifluoroethylene by the reaction of 1,1,2-trichloro-1,2,2-trifluoroethane with hydrogen in the presence of a catalyst system comprising 12–22% of Cu as well as a Group VIIIB element on a carbon support. WO 9729065 A1 discloses a process in which a gaseous feed of steam and a saturated hydrohalocarbon having a fluorine substituent and one or more further halogen substituents, e.g., 1,1,1,2-tetrafluoroethane, is passed through a heated reaction zone and the fluorinated alkene, e.g., trifluoroethylene, is recovered. French Patent 2,729,136 discloses a process, which enables the doping of the catalyst for stability. A stream of fluoroalkane containing $BF_3$ and, optionally N, is passed continuously over an $AlF_3$ catalyst at 400–600° C. Passing a mixture. of $CF_3CH_2F$ 59.8, N 59.9, and $BF_3$ 15.8 mmol/h over an $AlF_3$ catalyst at 470° C./1 atmosphere and 65 h gave a conversion of $CF_3CH_2F$ of 12.8 and 13.7%, and selectivity for $CF_2$:CHF of 94.5 and 98.5%, respectively; vs. 14.2%, 7.7%, 95.8%, and 97.4%, respectively., after 15 and 63 h in the absence of $BF_3$. In Japanese Patent No. JP 43-008454 trifluoroethylene is prepared. by a 1-step reaction of $CCl_2FCClF_2$ and hydrogen over a Pd or Pt catalyst at 200–300° C. A 1:2 molar $CCl_2FCClF_2$:hydrogen feed was passed through a quartz tube (20×700 mm.) containing 5% Pd—C with a space velocity of 144 L./l hr to give the following results: reaction temp., % $CCl_2FCClF_2$ conversion, and mole % trifluoroethylene in the product given—: 200° C., 60.0%, 65.3%; 250° C., 69.4%, 56.4&; 300° C., 86.5%, 30.8%, together with 39.2 mole % $CClF_2CHClF$. In Journal of Electroanalytical Chemistry (1997), 435 (1–2), 255–258 there is disclosed that chlorotrifluoroethene was the unique product described in the literature from the electroredeposition of 1,1,2-trichloro-1,2,2-trifluoroethane (R 113). Preliminary results on new electrosynthetic possibilities of the electroredeposition. of R 113 on Pb and Cd cathodes in MeOH—$H_2O$ solutions. containing. ammonium salts and different cations are reported. The essential result was that trifluoroethene, difluoroethene, difluoroethane and fluoroethane were produced instead of chlorotrifluoroethene when Pd2+ salts were added into the electrolyte. The use of a hydrogen diffusion anode permitted conducting the electrosynthesis in a monocompartimental cell without undesirable by-products. Japanese Patent publication JP 2002275106 relates to a Process for producing fluorinated aliphatic compounds by pyrolysis of perfluorocarboxylic acids and their halides and esters. The pyrolysis is carried out in the presence of a catalyst comprising a carrier most preferably chosen among active carbon, MgO, CaO, BaO, ZnO, $Al_2O_3$, NiO, and $SiO_2$ promoted with alkali metal halides selected from the series comprising fluorides, chlorides, bromides, iodides of sodium, potassium, rubidium, cesium at approximately. 100–450° C. to prepare fluorinated aliphatic compounds comprising perfluoroolefins, polyfluoroolefins and their derivatives, and optionally, in the presence of additional HF to form fluorinated aliphatic compounds comprising polyfluoroalkanes and their derivatives. Thus, pyrolysis of perfluorovaleric acid Me ester using $SiO_2$/KF as catalyst at 240° C. gave 95.1% perfluoro-2-butene.

Russian Patent RU 218814 Cl relates to a Thermal decomposition process for the integrated production of perfluorocarbons. The production. of industrially important fluorocarbons, in particular tetrafluoroethylene, hexafluoropropylene, and octafluorocyclobutane, is accomplished via the thermal decomposition of difluorochloromethane with steam and tetrafluorochloroethane. The pyrolyzate is subjected to tempering, freed of HCl (for the production. of hydrochloric acid), neutralized, compressed, and condensed in a three-step process receiving a polymerization inhibitor before the first and second condensation steps. From the second-step condensate, low-boiling substances are removed by rectification and tetrafluoroethylene is recovered. The bottoms fraction is combined with the first-step condensate and the resulting mixture is subjected to a multi-step rectification to yield fractions of difluorochloromethane/hexafluoropropylene and tetrafluorochloroethane/octafluorocyclobutane azeotropes, from which hexafluoropropylene and oectafluorocyclobutane are isolated. In the third condensation step, difluorochloromethane or indicated azeotropes are additionally. introduced. The third-step condensate is added to still fraction-first-step condensate mixture and, from the combined mixture before isolation of above-indicated azeotropes, the first tetrafluoroethylene-containing gases (which are transferred into the pyrolyzate compression stage) and then, optionally, trifluoroethylene are rectified into a light-boiling fraction. The tetrafluoroethylene concentration in the third-step condensate is maintained at 10–30%. In Chinese patent No. 1351903 hydrodechlorination catalysts for preparing trifluorochloroethylene and trifluoroethylene is composed of Ru (or Pd and Pt) and Cu as active compounds.; lanthanide-rich rare earth metal mixtures (or La) and lithium as modifiers; and coconut shell activated carbon as support. In WO 2004

080937 there is disclosed a process for manufacture of fluorinated monomers. The process is disclosed for the conversion of fluorocarbons into fluorinated unsaturated compounds useful as monomers or other chemical precursors, such as $C_2H_2F_2$. The process comprises reacting a hydrocarbon feed and a fluorocarbon feed in a high temperature reactor at a sufficiently high temperature and sufficiently short resident time to form a reaction product mixture having the fluorinated unsaturated compound as the major reaction product, and cooling it to a temperature sufficiently low to inhibit polymerization of the unsaturated compound. The reaction product may then be processed by removal of higher molecular weight compounds and acids and optionally separated into product components.

Despite these processes, there is a need for a relatively inexpensive and simple process for the production of trifluoroethylene and tetrafluoropropylene, and particularly one that does not require the use of hydrogen gas and is thereby enabled to avoid the major concern with safety related issues associated with the handling of hydrogen gas in large scale production.

SUMMARY OF THE INVENTION

The process of the invention comprises a process for producing a trifluoroethylene ($CF_2=CHF$) from 1,1,1,2-tetrafluoro-2-chloroethane (R124), 2,2-dichloro-1,1,1,2-tetrafluoroethane (R114a) or chloropentafluoroethane (R115), and tetrafluoropropylene ($CF_3-CF=CH_2$) from 1,1,1,2,2-pentafluoro-3-chloropropane (R235cb). or 1,1,1,2,2,-pentafluoro-3,3,-dichloropropane (R225ca). The process comprises contacting, in the presence of a suitable catalyst, the 1,1,1,2-tetrafluoro-2-chloroethane (R124), 2,2-dichloro-1,1,1,2-tetrafluoroethane (R114a) or chloropentafluoroethane (R115) reactant with a reducing agent selected from the group consisting of methane, methyl chloride and mixtures thereof, in a gas phase reaction to produce trifluoroethylene, or contacting, in the presence of a suitable catalyst, the 1,1,1,2,2-pentafluoro-3-chloropropane.(R235cb) or 1,1,1,2,2,-pentafluoro-3,3,-dichloropropane (R225ca) reactant with a reducing agent selected from the group consisting of methane, methyl chloride and mixtures thereof, in a gas phase reaction to produce tetrafluoropropylene. The reaction may be conducted in the presence of any suitable catalyst, preferably, nickel mesh, with or without a catalyst promoter, and is conducted in a suitable reaction vessel at a suitable time and temperature. The process is most preferably conducted with 1,1,1,2-tetrafluoro-2-chloroethane (R124) as the reactant for producing trifluoroethylene,

DETAILED DESCRIPTION OF INVENTION AND PREFERRED EMBODIMENTS

The novel process of the invention comprises a process for producing trifluoroethylene from 1,1,1,2-tetrafluoro-2-chloroethane (R124), 2,2-dichloro-1,1,1,2-tetrafluoroethane (R114a) or chloropentafluoroethane (R115), and most preferably 1,1,1,2-tetrafluoro-2-chloroethane, and for producing tetrafluoropropylene from 1,1,1,2,2-pentafluoro-3-chloropropane (R235cb) or 1,1,1,2,2,-pentafluoro-3,3,-dichloropropane (R225ca), the process comprising contacting, in the presence of a suitable catalyst, the 1,1,1,2-tetrafluoro-2-chloroethane, 2,2-dichloro-1,1,1,2-tetrafluoroethane or chloropentafluoroethane reactant with a reducing agent selected from the group consisting of methane, methyl chloride and mixtures thereof, in a gas or vapor phase reaction to produce trifluoroethylene, or contacting, in the presence of a suitable catalyst, the 1,1,1,2,2-pentafluoro-3-chloropropane. or 1,1,1,2,2,-pentafluoro-3,3,-dichloropropane reactant with a reducing agent selected from the group consisting of methane, methyl chloride and mixtures thereof, in a gas phase reaction to produce tetrafluoropropylene, The process of this invention comprises producing a product of the formula:

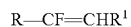

R—CF=CHR¹ wherein R is F or $CF_3$ and $R^1$ is F when R is F and is H when R is $CF_3$ by reacting a reactant of the formula:

$CF_3-R^2$ wherein $R^2$ is selected from

and

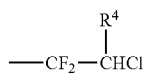

wherein $R^3$ is H, F or Cl and $R^4$ is H or Cl.

The reaction may be conducted in the presence of any suitable catalyst, preferably, nickel mesh, with or without a catalyst promoter, and is conducted in a suitable reaction vessel at a suitable time and temperature. The process is believed to follow a free radical pathway. Illustratively, in the case of 1,1,1,2-tetrafluoro-2-chloroethane as the reactant for producing trifluoroethylene, the C—Cl bond cleaves heterolytically to $CF_3CFH$ and Cl and is believed to proceed along the following reaction scheme.

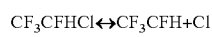

$CF_3CFHCl \leftrightarrow CF_3CFH + Cl$

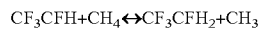

$CF_3CFH + CH_4 \leftrightarrow CF_3CFH_2 + CH_3$

$CF_3CFH_2 \rightarrow CF_2=CHF + HF$

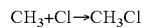

$CH_3 + Cl \rightarrow CH_3Cl$

The presence of the catalyst is believed to help the initiation step (first reaction) that is in equilibrium. In the case of 2,2-dichloro-1,1,1,2-tetrafluoroethane (R114a) as the reactant the product produced is a mixture of trfluoroethylene and $CF_2=CFCl$, (R13) and in the case of chloropentafluoroethane (R115) as the reactant the product is trfluoroethylene.

It has been discovered that methane and methyl chloride are selective reducing agents for producing trifluoroethylene from 1,1,1,2-tetrafluoro-2-chloroethane. (R124) 2,2-dichloro-1,1,1,2-tetrafluoroethane (R114a) or chloropentafluoroethane (R115) or producing tetrafluoropropylene from 1,1,1,2,2-pentafluoro-3-chloropropane. or 1,1,1,2,2,-pentafluoro-3,3,-dichloropropane. The selectivity of trifluoroethylene from 1,1,1,2-tetrafluoro-2-chloroethane can be as high as about 35%, and will generally be in the range of about 25 to about 35% selectivity, generally at conversion levels of 1,1,1,2-tetrafluoro-2-chloroethane of from about 75% up to 100%. The selectivity of tetrafluoropropylene from the reactants for producing it will generally be about 15 to 20%.

Any suitable reducing catalyst may be employed in the process of this invention. The novel process of this invention permits the use of relatively inexpensive catalysts, such as an alkali metal catalyst. It is preferred to employ as the catalyst for the reaction either a noble metal catalyst or nickel mesh. However, any suitable reduction catalyst may be employed, including but not limited to, Group VIII catalysts such as nickel, platinum and palladium catalysts, Group 1B catalysts such as silver and gold catalysts, as well as lanthanum and lanthanide catalyst. Any suitable alkali metal catalyst may be employed, such as a magnesium, calcium, barium and strontium catalyst. Especially preferred as a catalyst for the reaction is nickel mesh. The catalyst is preferably a supported catalyst and any suitable catalysts support, such as for example, alumina, activated carbon, and basic metal oxides such as BaO, MgO, CaO, Cu(II) oxide and Co(III) oxide may be employed. Further examples of suitable catalyst include Pd/C and Pd/alumina. It may also desirable to employ a suitable catalyst promoter, such as for example, $CsNO_3$, $Cu(NO_3)_2$, $Co(NO_3)_2$, and $Pd(NO_3)_2$. A preferred catalyst is nickel mesh catalyst, such as that available from Koch-Otto York Company, Parsippany, N.J. as Style 421, 1100 $m^2$/gm, mesh size 0.011 inch (0.028 cm).

The reaction is preferably conducted in the presence of air or some oxygen to prevent the formation of carbon as product and to thereby keep the catalyst surface clean of carbon deposition.

The reaction may be conducted at any suitable temperature, generally at a temperature in the range of from about 300° C. to about 800° C., more preferably at a temperature in the range of from about 350° C. to about 750° C., and even more preferably at a temperature in the range of from about 400° C. to about 700° C., and more preferably at a temperature of from about 600° C. to about 700° C.

The reaction may be conducted at any suitable pressure, generally at a pressure of from about 1 psig to about 300 psig (703.07 to 210,921 $kg/m^2$), preferably at a pressure of from about 1 psig to about 100 psig (703.07 to 70,307 $kg/m^2$), and more preferably at a pressure of from about 1 psig to about 10 psig (703.07 to 7030.7 $kg/m^2$).

The reaction contact time for the reactants may be any suitable contact time, generally a time of from about 1 sec. to about 120 sec., preferably a time of from about 1 sec. to about 60 sec., and most preferably a time of from about 1 sec. to about 30 sec.

Any suitable flow rate of the reactants may be employed, such as for example a flow rate of from about 5 $cm^3$/min (SCCM) to about 5000 $cm^3$/min, preferably a rate of from about 10 $cm^3$/min to about 1000 $cm^3$/min, and more preferably at a flow rate of from about 20 $cm^3$/min to about 100 $cm^3$/min.

The reaction may be conducted in any suitable reaction container or vessel, such as for example, Hastelloy®, Inconel®, Monel®, stainless steel, steel vessels, or in a Teflon lined reaction vessels.

The invention is illustrated by the following illustrative, but non-limiting examples.

EXAMPLES 1–5

In a typical reaction, a 1-inch diameter Monel® reactor was charged with 50 cc catalyst. The reactor was heated to 675° C. $CH_4$ or methyl chloride and 1,1,1,2-tetrafluoro-2-chloroethane (R124) were passed together from mass flow controllers into a preheater. The preheater temperature was kept at 350° C. The gas stream coming out of the preheater was passed through the catalyst bed at 675° C. for a specified period of time. An on-line GC and GCMS analyzed the reactor exit gases. Finally, the reactor exit was run into a 20% KOH solution at room temperature to eliminate any acid such as HF or HCl formed in-situ during the reaction. The exit gas mixture from the scrubber solution was then condensed to collect the products in liquid $N_2$. The desired product trifluoroethene, $CF_2$=CHF (R1123), product was then isolated from the mixture by distillation. The conditions and results of the Examples 1 to 4 are set forth in Table 1.

TABLE I

| Ex. No.[a] | Catalyst | Temp ° C. | $CH_4$ sccm[b] | $CF_3CFHCl$ sccm | Air sccm | % Conversion of $CF_3CFHCl$[c] | % Selectivity to $CF_2$=CHF[d] |
|---|---|---|---|---|---|---|---|
| 1 | Ni-mesh | 675 | 17 | 29 | 15 | 98 | 22 |
| 2[e] | Ni-mesh | 650 | $CH_3Cl$ 25 | 50 | 15 | 100 | 28 |
| 3 | Pd/C | 675 | 25 | 50 | 15 | 100 | 3 |
| 4 | Pd/Alumina | 675 | 20 | 40 | 15 | 78 | 6 |
| 5 | Pt/C | 675 | 20 | 40 | 15 | 78 | 6 |

[a]Reaction conditions: pressure, 10 psig; catalyst, 50 cc;
[b]sccm is standard cubic centimeter per minute;
[c]conversion is the ratio of moles of $CF_3CFHCl$ reacted to the total moles taken initially multiplied by 100;
[d]% selectivity is the ratio of moles of $CF_3CFHCl$ converted to $CF_2$=CHF to total moles of $CF_3CFHCl$ reacted multiplied by 100;
[e]Methyl chloride is used as the reducing agent instead of methane.

Table 1 shows results of reactions between 1,1,1,2-tetrafluoro-2-chloroethane (R124) and methane (Example Nos. 1, 2, 3, and 4) and methyl chloride (Example No. 2) using different catalysts. Ni-mesh is the most active catalyst, 22% selectivity to trifluoroethylene (R1123) at a 1,1,1,2-tetrafluoro-2-chloroethane (R124), conversion level of 98% is achieved. The yield to trifluoroethene (R1123) increased to 28% when methane is replaced by methyl chloride in the presence of Ni-mesh catalyst (Example No. 2). The major by-products were $CF_3CFH_2$ (R134a), CO, $CO_2$, and $CF_3Cl$ (R13).

EXAMPLES 6–14

Process parameters for the process of this invention, employing the preferred Ni-mesh catalyst, were studied in Examples 6 to 14 as described in the following Table 2.

TABLE 2

| Ex. No.[a] | Catalyst | Temp ° C. | $CH_3Cl$ sccm | $CF_3CFHCl$ sccm[b] | Air Sccm | % Conversion of $CF_3CFHCl$[c] | % Selectivity to $CF_2$=$CHF$[d] |
|---|---|---|---|---|---|---|---|
| 6 | Ni-mesh | 600 | 25 | 50 | 15 | 85 | 16 |
| 7 | Ni-mesh | 650 | 25 | 50 | 15 | 100 | 28 |
| 8 | Ni-mesh | 700 | 25 | 50 | 15 | 100 | 21 |
| 9 | Ni-mesh | 725 | 25 | 50 | 15 | 78 | 14 |
| 10 | Ni-mesh | 650 | 25 | 30 | 15 | 100 | 26 |
| 11 | Ni-mesh | 650 | 25 | 70 | 15 | 94 | 21 |
| 12 | Ni-mesh | 650 | 25 | 102 | 15 | 83 | 14 |
| 13 | Ni-mesh | 650 | 25 | 50 | 10 | 96 | 22 |
| 14 | Ni-mesh | 650 | 25 | 50 | None | 100 | 34[f] |

[a]Reaction conditions: pressure, 10 psig; catalyst, 50 cc;
[b]sccm is standard cubic centimeter per minute;
[c]conversion is the ratio of moles of $CF_3CFHCl$ reacted to the total moles taken initially multiplied by 100;
[d]% selectivity is the ratio of moles of $CF_3CFHCl$ converted to $CF_2$=$CHF$ to total moles of $CF_3CFHCl$ reacted multiplied by 100;
[e]No Air is used.
[f]The yield to trifluoroethylene (R1123) in the absence of air was 34%; however, at this conditions, the major byproduct was 23% of carbon.

Table 2 shows results of important process parameter studies. Important parameters such as temperature, flow rate of 1,1,1,2-tetrafluoro-2-chloroethane (R124) and flow rate of air were observed. The reaction is optimized under the conditions given in Table 2, Example No. 7. The highest yield to trifluoroethene (R1123) (34%) was obtained under the conditions given in Table 2, Example No. 14, where the reaction is performed in the absence of air. Although the yield was high, the major problem associated with this condition was the formation of 23% of carbon which eventually killed the catalytic activity after 16 hr of run time. On the contrary, in the presence of air, the catalyst was active for at least 300 hrs. The presence of air is highly desirable to burn out C to $CO_2$ keeping the catalyst surface clean of carbon deposition.

EXAMPLE 15

R124 was passed through a 1-inch Monel® tubing packed with 50–100 cc of Ni-mesh as the catalyst at 675° C. with a contact time of 1–50 secs at 7–15 psig pressure. A 1-wt % $O_2$ was added to the feed stream to reduce the carbon formation, which is the major product in the absence of air/$O_2$. At a 98% 1,1,1,2-tetrafluoro-2-chloroethane, (R124), conversion level, 22-mol % yield to trifluoroethylene (R1123) was achieved. The major by products are 1,1,1,2-tetrafluoroethane (R134a), $CO_2$, and $CF_3Cl$ (R13).

EXAMPLES 16–19

Employing the process parameters as set forth in Example 1, but employing as the reactants 1,1,1,2,2-pentafluoro-3-chloropropane (Example 16 and 17) or 1,1,1,2,2,-pentafluoro-3,3,-dichloropropane (Examples 18 and 19) and employing as the reducing agent methane (Examples 16 and 18) or methyl chloride (Examples 17 and 19), 1,1,1,2-tetrafluoropropylene is produces in yields of about 15% in Examples 16 and 17, and about 19% in Examples 18 and 19.

The reaction mechanism of this invention is studied and believed to follow a free radical pathway. Illustratively, in the case of $CF_3CFHCl$ (R124), the C—Cl bond cleaves heterolytically to $CF_3CFH$ and Cl. In the first step, $CF_3CFHCl$ is reduced to 1,1,1,2-tetrafluoroethane (R134a) by methane or methyl chloride. Eventually, in the second step, 1,1,1,2-tetrafluoroethane (R134a) is dehydrofluorinated to trifluoroethylene (R1123).

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

What is claimed is:

1. A process for producing a compound of the formula:

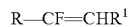

R—CF=$CHR^1$ wherein R is selected from the group consisting of F and $CF_3$, and $R^1$ is F when R is F and $R^1$ is H when R is $CF_3$, the process comprising contacting, in the presence of a catalyst, a reactant of the formula:

$CF_3$—$R^2$ wherein $R^2$ is selected from the group consisting of

—CF
|
$R^3$ and

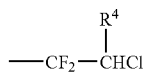

—$CF_2$—$CHCl$
        |
        $R^4$ wherein $R^3$ is selected from the group consisting of H, F and Cl and $R^4$ is selected from the group consisting of H and Cl,
with a reducing agent selected from the group consisting of methane, methyl chloride and mixtures thereof, in a gas phase reaction.

2. A gas phase reaction process for producing trifluoroethylene comprising contacting, in the presence of a catalyst, 1,1,1,2-tetrafluoro-2-chloroethane with a reducing agent wherein the reducing agent is methane.

3. A gas phase reaction process for producing trifluoroethylene comprising contacting, in the presence of a catalyst, 1,1,1,2-tetrafluoro-2-chloroethane with a reducing agent wherein the reducing agent is methyl chloride.

4. The process according to claim 1 wherein the catalyst comprises a catalyst selected from the group consisting of a noble metal catalyst and-nickel mesh catalyst.

5. The process according to claim 2 wherein the catalyst comprises a catalyst selected from the group consisting of a noble metal catalyst and nickel mesh catalyst.

6. The process according to claim 3 wherein the catalyst comprises a catalyst selected from the group consisting of a noble metal catalyst and nickel mesh catalyst.

7. The process according to claim 1 wherein the catalyst is nickel mesh catalyst.

8. The process according to claim 2 wherein the catalyst is nickel mesh catalyst.

9. The process according to claim 3 wherein the catalyst is nickel mesh catalyst.

10. The process according to claim 1 wherein the reaction is conducted in the presence of air or oxygen.

11. The process according to claim 2 wherein the reaction is conducted in the presence of air or oxygen.

12. The process according to claim 3 wherein the reaction is conducted in the presence of air or oxygen.

13. The process according to claim 7 wherein the reaction is conducted in the presence of air or oxygen.

14. The process according to claim 8 wherein the reaction is conducted in the presence of air or oxygen.

15. The process according to claim 9 wherein the reaction is conducted in the presence of air or oxygen.

16. The process according to claim 1 wherein the reactant is selected from the group consisting of 1,1,1,2-tetrafluoro-2-chloroethane, 2,2-dichloro-1,1,1,2-tetrafluoroethane and chloropentafluoroethane and the product is trifluoroethylene.

17. The process according to claim 4 wherein the reactant is selected from the group consisting of 1,1,1,2-tetrafluoro-2-chloroethane, 2,2-dichloro-1,1,1,2-tetrafluoroethane, and chloropentafluoroethane, and the product is trifluoroethylene.

18. The process according to claim 7 wherein the reactant is selected from the group consisting of 1,1,1,2-tetrafluoro-2-chloroethane, 2,2-dichloro-1,1,1,2-tetrafluoroethane, and chloropentafluoroethane, and the product is trifluoroethylene.

19. The process according to claim 10 wherein the reactant is selected from the group consisting of 1,1,1,2-tetrafluoro-2-chloroethane, 2,2-dichloro-1,1,1,2-tetrafluoroethane, and chloropentafluoroethane, and the product is trifluoroethylene.

20. The process according to claim 10 wherein the catalyst is nickel mesh catalyst, the reactant is 1,1,1,2-tetrafluoro-2-chloroethane, the reaction is conducted in the presence or air or oxygen, the reaction is conducted at a temperature of from about 600° C. to about 700° C., the product is trifluoroethylene, and the selectivity of trifluoroethylene production is at least about 25%.

* * * * *